(12) United States Patent
DeJovin et al.

(10) Patent No.: US 8,231,885 B2
(45) Date of Patent: Jul. 31, 2012

(54) COMPOUNDS, FORMULATIONS, AND METHODS FOR AMELIORATING TELANGIECTASIS

(75) Inventors: Jack A. DeJovin, New Brunswick, NJ (US); Isabelle Jean DeJovin, New Brunswick, NJ (US)

(73) Assignee: Galderma Laboratories Inc., Fort Worth, TX (US)

( * ) Notice: Subject to any disclaimer, the term of this patent is extended or adjusted under 35 U.S.C. 154(b) by 364 days.

(21) Appl. No.: 12/544,663

(22) Filed: Aug. 20, 2009

(65) Prior Publication Data

US 2010/0021402 A1 Jan. 28, 2010

Related U.S. Application Data

(63) Continuation-in-part of application No. 11/449,079, filed on Jun. 8, 2006, now Pat. No. 7,838,563, which is a continuation-in-part of application No. 10/853,585, filed on May 25, 2004, now Pat. No. 7,439,241.

(60) Provisional application No. 60/473,611, filed on May 27, 2003.

(51) Int. Cl.
| | |
|---|---|
| *A61K 8/00* | (2006.01) |
| *A61K 8/02* | (2006.01) |
| *A61K 33/24* | (2006.01) |
| *A61K 9/56* | (2006.01) |
| *A61K 31/135* | (2006.01) |
| *A61K 31/415* | (2006.01) |
| *A61K 8/18* | (2006.01) |
| *A01N 33/02* | (2006.01) |
| *A01N 43/60* | (2006.01) |

(52) U.S. Cl. ......... 424/401; 424/617; 424/459; 424/59; 514/249; 514/402; 514/649; 514/651

(58) Field of Classification Search ............... 424/459, 424/617, 776, 59, 401; 514/249, 402, 649, 514/651
See application file for complete search history.

(56) References Cited

U.S. PATENT DOCUMENTS

| | | | |
|---|---|---|---|
| 4,256,763 A | 3/1981 | McHugh | |
| 4,285,967 A | 8/1981 | Gubernick et al. | |
| 5,720,962 A | 2/1998 | Ivy et al. | |
| 5,916,574 A | 6/1999 | Fried et al. | |
| 6,117,877 A | 9/2000 | Fogel | |
| 6,846,499 B2 * | 1/2005 | El Mogy | 424/776 |
| 2006/0294614 A1 * | 12/2006 | Pausch | 800/18 |
| 2009/0061020 A1 * | 3/2009 | Theobald et al. | 424/617 |

FOREIGN PATENT DOCUMENTS

| | | |
|---|---|---|
| WO | WO 96/13267 | 5/1996 |
| WO | 2004105703 A | 12/2004 |
| WO | 2005002580 | 1/2005 |
| WO | 2005010025 A | 2/2005 |

OTHER PUBLICATIONS

Material Safety Data Sheet, pp. 1-2, (Mar. 1997).
Alfonso R. Gennaro., Remington: Practice of, 19th Edition, Chapter 52, pp. 880, 884, (1995).
Rebora, Alfredo, "The Management of Rosacea", Am. J. Clin. Dermatol. 2002; 3 (7); pp. 489-496.
Lindgren, et al., "Effects of Some Antihypertensive Drugs on Cutaneous Blood Flow and Inflammatory Skin Responses Following Allergen Challenge in Guinea Pigs," Pharmacology and Toxicology, 1987, vol. 60, pp. 364-367.
Guarrera, et al., "Flushing in Rosacea: A Possible Mechanism," Archives of Dermatological Research, 1982, vol. 272, pp. 311-316.
Burke, et al., "Preclinical Evaluation of Brimonidine," Survey of Ophthalmology Inc., 1996, vol. 41, pp. S9-S18.
Nielsen, et al., "Postjunctional alpha-2-adrenoceptors mediate vasoconstriction in human subcutaneous resistance vessels," British Journal of Pharmacology, 1989, vol. 97, pp. 829-834.

* cited by examiner

*Primary Examiner* — Blessing Fubara
(74) *Attorney, Agent, or Firm* — Hoffmann & Baron, LLP

(57) ABSTRACT

Methods, compounds, and topical formulations for treatment of telangiectasias are disclosed. The methods comprise topically applying a composition comprising an α-adrenergic receptor agonist to telangiectatic skin. Amelioration of telangiectasia symptoms begins within minutes after topical application of a disclosed composition. A single application can significantly lessen telangiectasia discoloration for at least about 2 hours.

22 Claims, No Drawings

COMPOUNDS, FORMULATIONS, AND METHODS FOR AMELIORATING TELANGIECTASIS

RELATED U.S. APPLICATIONS

The present application is a continuation-in-part of U.S. patent application Ser. No. 11/449,079 filed Jun. 8, 2006 now U.S. Pat. No. 7,838,563, which is a continuation-in-part of U.S. patent application Ser. No. 10/853,585 filed May 25, 2004 now U.S. Pat. No. 7,439,241, which claims priority to U.S. Provisional Patent Application No. 60/473,611, filed May 27, 2003. The contents of these applications are hereby incorporated by reference in their entireties.

FIELD

The present teachings are directed to compositions and methods for treatment of telangiectasias.

BACKGROUND

Telangiectasias are highly prevalent skin disorders. Telangiectasias are visible small, red, purple or blue surface blood vessels that can be located on the face, upper chest, neck or other parts of the body. Telangiectatic blood vessels, which can include swollen blood vessels, spider veins, red dermal patches, purple dermal patches, or blue dermal patches are abnormal and are not necessary for any essential body function.

Telangiectatic blood vessels can appear with or without a preceding or concurrent skin or internal disease. Telangiectasias can develop anywhere within the body, but can be most easily seen in the skin. Telangiectasias include essential or primary telangiectasias, which include blood vessel dilations of unknown etiology. Generalized essential telangiectasias (GET) exhibit a widespread distribution pattern over the body. Other primary telangiectases include angioma serpiginosum, ataxia telangiectasia, angiomas and spider naevi. Some other examples of conditions, syndromes, diseases and disorders which can include telangiectasias are CREST Syndrome (acronym for Calcinosis, Raynaud's phenomenon, Esophageal dysfunction, Sclerodactyl), and Telangiextasis), hereditary hemorrhagic telangiectasia (Osler-Weber-Rendu Syndrome), Ataxia-telangiectasia, rosacea (also known as acne rosacea), basal cell carcinoma, scleroderma, unilateral nevoid telangiectasia, Cutis marmorata telangiectatica congenita, and hereditary hemorrhagic telangiectasia.

A telangiectasia can be a symptom of rosacea, However, rosacea also encompasses erythema, and is, accordingly, a phenomenon distinct from a telangiectasia.

Current treatments for ameliorating telangiectasias include laser therapy and electro-optical synergy (ELOS), which combines intense pulsed optical energy and conducted bipolar radiofrequency (RF) energy into a single pulse (Sadick, N S et al., J. Drugs Dermatolog. 4: 181-186, 2005).

SUMMARY

The present inventors have developed formulations and treatment methods for mitigating telangiectasias. The methods include topically applying a formulation comprising an α-adrenergic receptor agonist to an affected area of the skin of a subject in need of treatment of a telangiectasia. Topical application of an α-adrenergic receptor agonist leads to a reduction in the visibility of telangiectatic blood vessels directly at and adjacent to the site of application. A formulation which can be used in the methods can further comprise additional components such as an excipient. In various aspects, an α-adrenergic receptor agonist can be applied to the skin in a topical skin formulation that is effective for mitigating a telangiectasia but does not induce serious systemic side effects in the patient.

Accordingly, in various aspects, the present teachings disclose methods of ameliorating telangiectatic skin. The methods comprise topically administering to the skin of a subject in need of treatment a composition comprising at least one active ingredient selected from an α-adrenergic receptor agonist, a prodrug thereof, a pharmaceutically acceptable salt thereof, a hydrate thereof, a solvate thereof and a combination thereof. In various aspects, a composition is administered in an amount effective for mitigating a telangiectasia. An amount effective for mitigating a telangiectasia can be an amount locally effective for amelioration of telangiectasia upon topical administration. In addition, in various configurations, an effective amount of an α-adrenergic receptor agonist for ameliorating a telangiectasia can be non-restrictive with regard to other skin care and cosmetic products. Accordingly, a formulation comprising an α-adrenergic receptor agonist can be compatible with, e.g., separate application of make-up. Furthermore, in some configurations, an α-adrenergic receptor agonist can be comprised by a skin care or cosmetic product, so that the user can simultaneously receive the benefits of both suppressing a telangiectasia as well as masking, coloring and/or cleansing skin by application of a single product. In various configurations, a subject can be a mammal, such as a human, a farm animal, or a companion animal.

In various configurations, an α-adrenergic receptor agonist which can be comprised by a composition described herein can be any α-adrenergic receptor agonist, as well as active solvates, hydrates, prodrugs such as esters, stereoisomers including enantiomers, polymorphic forms, and crystalline forms thereof. In addition, various formulations can comprise at least one α1-adrenergic receptor agonist, at least one α2-adrenergic receptor agonist, or a combination thereof. In various configurations, an α-adrenergic receptor agonist can be a selective α1-adrenergic receptor agonist, a selective α2-adrenergic receptor agonist, or an α-adrenergic receptor agonist which is non-selective for either type of α-adrenergic receptor. Accordingly, some α-adrenergic receptor agonists which can be used in the disclosed methods and compositions include amphetamine, apraclonidine, brimonidine, clonidine, dexmedetomidine, dextroamphetamine, dopamine, I-dobutamine, ephedrine, epinephrine, epinine (N-methyl-dopamine), ethylnorepinephrine, guanabenz, guanfacine, levarterenol, lofexidine, mephentermine, metaraminol, methamphetamine, methoxamine, α-methyldopa, α-methylnorepinephrine, methylphenidate, mivazerol, mitodrine, moxonidine, naphazoline, norepinephrine, norphenylephrine, oxymetazoline, pemolinepropylhexedrine, phenylephrine, phenylpropanolamine, propylhexedrine, tetrahydrozoline, tizanidine and xylometazoline.

In various configurations, an α-adrenergic receptor agonist which can be comprised by a formulation and used in methods of the present teachings can have the structure of a compound shown below:

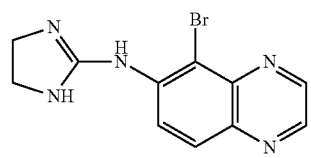

(5-Bromo-quinoxalin-6-yl)-(4,5-dihydro-1H-imidazol-2-yl)-amine (Brimonidine)

-continued

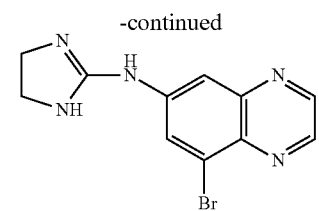

(8-Bromo-quinoxalin-6-yl)-(4,5-dihydro-1H-imidazol-2-yl)-amine

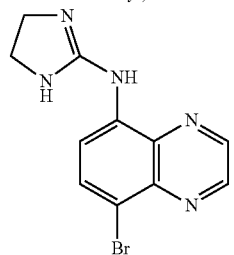

(8-Bromo-quinoxalin-5-yl)-(4,5-dihydro-1H-imidazol-2-yl)-amine

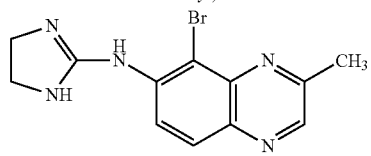

(5-Bromo-3-methyl-quinoxalin-6-yl)-(4,5-dihydro-1H-imidazol-2-yl)-amine

In some configurations, an α-adrenergic receptor agonist which can be comprised by a formulation and used in methods of the present teachings can have the structure of a compound shown in Formula I below:

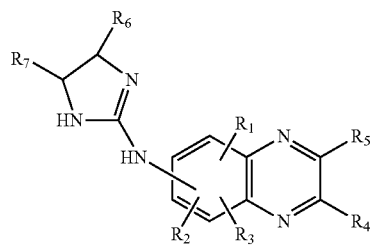

I wherein each of R1, R2, and R3 is independently hydrogen, halogen, alkyl, or alkoxy, wherein, the alkyl can be an unsubstituted alkyl such as a $C_1$-$C_{20}$ alkyl, and the alkoxy can be an unsubstituted alkoxy such as a $C_1$-$C_{20}$ alkoxy; each of R4 and R5 can be, independently, hydrogen, alkyl, alkyl, or alkoxy, wherein the alkyl can be an unsubstituted alkyl such as a $C_1$-$C_{20}$ alkyl, and the alkoxy can be an unsubstituted alkoxy such as a $C_1$-$C_{20}$ alkoxy and wherein each of R6 and R7 is independently hydrogen, nitro, alkyl, or alkoxy, wherein the alkyl can be an unsubstituted alkyl such as a $C_1$-$C_{20}$ alkyl, and the alkoxy can be an unsubstituted alkoxy such as a $C_1$-$C_{20}$ alkoxy; and wherein a substituent designated with a line segment extending into a ring structure indicates that the substitutent can attach to the ring at any available position on the ring. In some aspects of compounds of Formula I, R6 and R7 can both be hydrogen. In some other aspects, R4 and R5 can both be hydrogen.

In some configurations, an α-adrenergic receptor agonist which can be comprised by a formulation and used in methods of the present teachings can have the estructur of a compound shown in Formula II below:

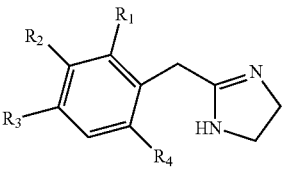

II wherein each of $R_1$, $R_2$, and $R_4$ can be, independently, hydrogen or alkyl wherein the alkyl can be an unsubstituted alkyl such as a $C_1$-$C_{20}$ alkyl, and $R_2$ can be hydrogen or hydroxyl.

In some configurations, an α-adrenergic receptor agonist which can be comprised by a formulation and used in methods of the present teachings can have the structure of a compound shown in Formula III below:

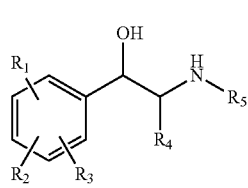

III wherein each of $R_1$, $R_2$, and $R_3$ can be, independently, hydrogen, hydroxy or methoxy, and each of $R_4$ and $R_5$ can be, independently, hydrogen or alkyl, such as a $C_1$-$C_{20}$ alkyl.

In some configurations, an α-adrenergic receptor agonist which can be comprised by a formulation and used in methods of the present teachings can have the structure of a compound shown in Formula IV below:

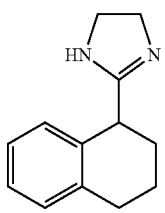

IV

In some configurations, an α-adrenergic receptor agonist which can be comprised by a formulation and used in methods of the present teachings can have the structure of a compound shown in Formula V below:

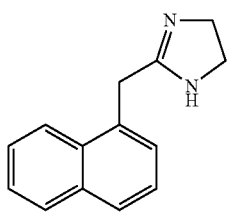

V

In various aspects, a composition of the present teachings comprising an α-adrenergic receptor agonist can further comprise a pharmaceutically acceptable carrier. In some aspects, a composition can be a spray, a mist, a low viscosity aqueous and/or alcoholic liquid, an aerosol, a lotion, a foam, a gel, a cream, an ointment, a paste, an unguent, an emulsion, a liposomal suspension, a colloid or a combination thereof, while in other aspects, a composition can be formulated as a cosmetic, a foundation, a moisturizer, or a sun-blocking agent. As used herein, the term "low viscosity aqueous liquid" refers to a liquid having a viscosity of less than about 3 centipoise at 25° C.

In some configurations, a composition comprising an α-adrenergic receptor agonist can further comprise a pharmaceutically acceptable carrier, such as an aqueous gel comprising water and a water-gelling amount of a pharmaceutically acceptable gelling agent selected from a carbomer, a glycerine polyacrylate, and a mixture thereof, and can be a spray, a mist, an aerosol, a lotion, a foam, a gel, a cream, an ointment, a paste, an unguent, an emulsion, a liposomal suspension, a colloid or a combination thereof. A cream or an ointment can comprise stearic acid, stearyl alcohol, cetyl alcohol, glycerin, and/or water.

In various configurations, a topical composition can comprise an α-adrenergic receptor agonist, a pharmaceutically acceptable salt or a combination thereof in an amount from at least about 0.001% w/w up to about 10% w/w. In some configurations, a composition can have a pH of from about 5 to about 8. In various aspects, a composition of the present teachings can further comprise a preservative, a local anesthetic, and/or a skin humectant.

In some aspects, a topical composition for mitigating a telangiectasia can comprise at least one first active ingredient selected from an α-adrenergic receptor agonist, a pharmaceutically acceptable salt thereof and a combination thereof, and at least one second active pharmaceutical ingredient selected from an antibiotic, a non-antibiotic chemically modified tetracycline, a steroid, a retinoid, and an anti-fungal agent. In various configurations, a second active pharmaceutical ingredient can be azelaic acid, benzoyl peroxide, isotretinoin, an antibiotic, a non-antibiotic chemically modified tetracycline, a pharmaceutically acceptable salt thereof or a combination thereof. In some configurations, an antibiotic can be clindamycin, doxycycline, erythromycin, metronidazole, sulfacetamide, tetracycline, or a combination thereof. Furthermore, a non-antibiotic chemically modified tetracycline can be, for example, a tetracycline derivative such as, for example, 4-de(dimethylamino)tetracycline (GMT-1), tetracyclinonitrile (CMT-2), 6-demethyl-6-deoxy-4-de(dimethylamino)tetracycline (CMT-3), 4-de(dimethylamino)-7-chlorotetracycline (CMT-4), tetracycline pyrazole (CMT-5) 4-hydroxy-4-de(dimethylamino)tetracycline (CMT-6), 4-de(dimethylamino)-12.alpha.-deoxytetracycline (CMT-7), 6-.alpha.-deoxy-5-hydroxy-4-de(dimethylamino)tetracycline (CMT-8), 4-de(dimethylamino)-12.alpha.-deoxyanhydrotetracycline (CMT-9), or 4-de(dimethylamino) minocycline (CMT-10), (see, e.g., U.S. Pat. No. 7,014,858 to Ashley; Islam, M. M., et al., Amer. J. Path. 163: 1557-1566, 2003). A topical composition can comprise the first active ingredient in a prescription strength concentration or in an over-the-counter strength concentration. In some configurations of methods of the present teachings, an antibiotic can be administered in an amount effective for treatment of telangiectasia.

In various aspects of the present teachings, an amount of a composition effective for amelioration of a telangiectasia can be an amount which ameliorates a telangiectasia within about 2 minutes after the administering, within about 5 minutes after the administering, or within about 10 minutes after the administering. In various other aspect, an amount effective for amelioration of a telangiectasia can be an amount which ameliorates the telangiectasia for up to about 2 hours, up to about 4 hours, up to about 8 hours, up to about 12 hours, up to about 18 hours, up to about 24 hours, or longer.

Aspects of a telangiectasia which can be ameliorated using the present methods include, for example, swelling of blood vessels, enlarged, dilated and/or visible spider veins, and red, purple or blue patches on the skin resulting from dilated blood vessels.

In certain aspects of the present teachings, the present inventors have developed pharmaceutical packages for treatment of symptoms of telangiectasia. A package of these aspects can comprise a first active ingredient selected from at least one α-adrenergic receptor agonist, a pharmaceutically acceptable salt thereof and a combination thereof, in an amount effective for amelioration of a telangiectasia. A package can further comprise a second active pharmaceutical ingredient selected from azelaic acid, benzoyl peroxide, isotretinoin, an antibiotic, a pharmaceutically acceptable salt thereof and a combination thereof, and furthermore can comprise a pharmaceutically acceptable carrier, a container, and instructions for use of the topical composition.

In some configurations, methods of treating symptoms of telangiectasia can comprise selecting a first active ingredient on the basis of it having α-adrenergic receptor agonist activity, and topically administering to the skin of a patient in need of treatment a composition comprising a first active ingredient selected from at least one α-adrenergic receptor agonist, a pharmaceutically acceptable salt thereof and a combination thereof, in an amount effective for amelioration of a telangiectasia. In other configurations, methods of treating telangiectasias can comprise selecting the first active ingredient on the basis of it having telangiectasia-ameliorating activity, or on the basis of having both αadrenergic receptor agonist activity and telangiectasia-ameliorating activity.

DETAILED DESCRIPTION

The present inventors describe herein compounds, compositions, formulations, and methods for treating telangiectasias. The methods comprise topically administering to the skin directly upon or adjacent to a telangiectasia, a composition comprising an α-adrenergic receptor agonist. No special preparation of the skin is required prior to administration of a composition, although cleansing of the skin prior to administration can enhance effectiveness.

As used herein, the term "telangiectasia" refers to a visible, permanent abnormal dilation of blood vessels, such as arterioles and venules. A visible blood vessel is a blood vessel visually discernable as a line to an observer without the aid of magnifying equipment (other than spectacles normally used by the observer). In various aspects, a telangiectatic blood vessel can have a diameter of at least about 0.5 mm. Telangiectasias can be associated with numerous conditions, syndromes, diseases and disorders. For example, a facial telangiectasia can be associated with age, sun exposure, and alcohol use. Other diseases, disorders, conditions and syndromes associated with telangiectasias include, in non-limiting example, scleroderma, hereditary hemorrhagic telangiectasia (Olser-Rendu syndrome), Ataxia-Telangiectasia, spider angioma, cutis marmorata telangiectasia congenita, Bloom syndrome, Klippel-TrenaunayWeber syndrome, Sturge-Weber disease, Xeroderma pigmentosa, Nevus flammeus, Generalized essential telangiectasias (GET), angioma serpiginosum, ataxia telangiectasia, spider naevi, CREST Syndrome, hereditary hemorrhagic telangiectasia (Osler-Weber-Rendu Syndrome), ataxia-telangiectasia, basal cell carcinoma, scleroderma, unilateral nevoid telangiectasia, and cutis marmorata telangiectatica congenita. In addition, in some aspects, a telangiectasia can be associated with rosacea, while in certain alternative aspects, a telangiectasia can be a telangiectasia not associated with rosacea.

α-adrenergic receptor agonists of the present teachings include any α-adrenergic receptor agonist known to skilled artisans. In some aspects, an α-adrenergic receptor agonist can be an α-adrenergic receptor agonist selective for α1-adrenergic receptors, an α-adrenergic receptor agonist selective for α2-adrenergic receptors, or an α-adrenergic receptor agonist non-selective for either α1 or α2-adrenergic receptors. As used herein, a selective α1-adrenergic receptor agonist is an agonist for which the $EC_{so}$ with respect to an α1-adrenergic receptor is less than the $EC_{so}$ with respect to an α2-adrenergic receptor, while a selective α2-adrenergic receptor agonist is an agonist for which the $EC_{so}$ with respect to an α2-adrenergic receptor is less than the $EC_{so}$ with respect to an α1-adrenergic receptor, wherein the $EC_{so}$ for an agonist is defined as the molar concentration of the agonist which produces 50% of the maximum possible response of a receptor to that agonist. Some non-limiting examples of αadrenergic receptor agonists which can be used in the present compositions and methods include: amphetamine, apraclonidine, brimonidine, clonidine, clonidine, dexmedetomidine, dextroamphetamine, dopamine, I-dobutamine, ephedrine, epinephrine, epinine (N-methyl-dopamine), ethylnorepinephrine, guanabenz, guanfacine, levarterenol, lofexidine, mephentermine, metaraminol, methamphetamine, methoxamine, α-methyldopa, α-methylnorepinephrine, methylphenidate, mivazerol, mitodrine, moxonidine, naphazoline, norepinephrine, norphenylephrine, oxymetazoline, pemolinepropylhexedrine, phenylephrine, phenylpropanolamine, propylhexedrine, tetrahydrozoline, tizanidine, xylometazoline, (8-bromo-quinoxalin-6-yl)-(4,5-dihydro-1H-imidazol-2-yl)-amine, (8-bromo-quinoxalin-5-yl)-(4,5-dihydro-1H-imidazol-2-yl)-amine, (5-bromo-3-methyl-quinoxalin-6-yl)-(4,5-dihydro-1H-imidazol-2-yl)-amine, (5-bromo-2-methoxy-quinoxalin-6-yl)-(4,5-dihydro-1H-imidazol-2-yl)-amine, (4,5-dihydro-1H-imidazol-2-yl)-(8-methyl-quinoxalin-6-yl)-amine, and (4,5-dihydro-1H-imidazol-2-yl)-quinoxalin-5-yl-amine, Compositions of the present teachings include one or more α-adrenergic receptor agonists, prodrugs thereof, pharmaceutically acceptable salts thereof, hydrates thereof, solvates thereof and combinations thereof.

In one aspect, an α-adrenergic agonist can have a structure set forth in Formula I:

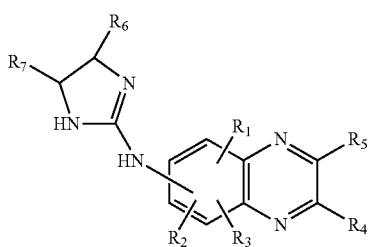

I wherein each of $R_1$, $R_2$, and $R_3$ can be, independently, hydrogen, halogen, alkyl, or alkoxy, wherein the alkyl can be an unsubstituted alkyl such as a $C_1$-$C_{20}$ alkyl, and the alkoxy can be an unsubstituted alkoxy such as a $C_1$-$C_{20}$ alkoxy; each of $R_4$ and $R_5$ is independently hydrogen, alkyl, or alkoxy; each of $R_6$ and $R_7$ is independently hydrogen, nitro, alkyl or alkoxy, wherein the alkyl can be an unsubstituted alkyl such as a $C_1$-$C_{20}$ alkyl, and the alkoxy can be an unsubstituted alkoxy such as a $C_1$-$C_{20}$ alkoxy; and wherein a substituent designated with a line segment extending into a ring structure indicates that the substituent can attach to the ring at any available position on the ring. In a certain aspects, in compounds of Formula I, $R_6$ and $R_7$ can both be hydrogen. In another other aspects, $R_4$ and $R_5$ can both be hydrogen.

In some other aspects, an α-adrenergic agonist can have a structure set forth in Formula Ia:

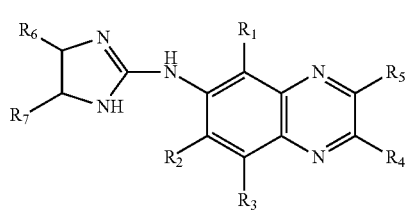

Ia wherein each of $R_1$, $R_2$, and $R_3$ is independently hydrogen, halogen, alkyl, or alkoxy, wherein the alkyl can be an unsubstituted alkyl such as a $C_1$-$C_{20}$ alkyl, and the alkoxy can be an unsubstituted alkoxy such as a $C_1$-$C_{20}$ alkoxy; each of $R_4$ and $R_5$ can be, independently, hydrogen, alkyl or alkoxy, wherein the alkyl can be an unsubstituted alkyl such as a $C_1$-$C_{20}$ alkyl, and the alkoxy can be an unsubstituted alkoxy such as a $C_1$-$C_{20}$ alkoxy; and each of $R_6$ and $R_7$ can be, independently, hydrogen, nitro, alkyl, or alkoxy, wherein the alkyl can be an unsubstituted alkyl such as a $C_1$-$C_{20}$ alkyl, and the alkoxy can be an unsubstituted alkoxy such as a $C_1$-$C_{20}$ alkoxy. In some aspects, in compounds of Formula Ia, $R_6$ and $R_7$ can both be hydrogen. In other aspects, $R_4$ and $R_5$ can both be hydrogen. In still other aspects, in compounds of Formula Ia, $R_2$, and $R_3$ can both be hydrogen and $R_1$ can be a halogen, such as bromo.

In some other aspects, an α-adrenergic agonist can have a structure set forth in Formula Ib:

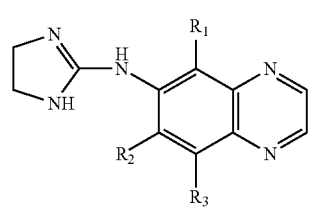

Ib wherein each of $R_1$, $R_2$, and $R_3$ is independently hydrogen, halogen, alkyl, or alkoxy, wherein, the alkyl can be an unsubstituted alkyl such as a $C_1$-$C_{20}$ alkyl, and the alkoxy can be an unsubstituted alkoxy such as a $C_1$-$C_{20}$ alkoxy. In one aspect, the compounds of Formula Ib, $R_2$, and $R_3$ can both be hydrogen and $R_1$ can be a halogen, such as a bromo.

In some other aspects, an α-adrenergic agonist can have a structure set forth in Formula Ic:

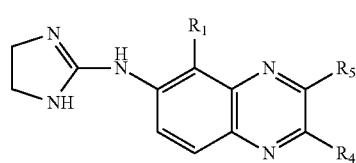

Ic wherein $R_1$ is hydrogen, halogen, alkyl, or alkoxy. In various aspects, the alkyl can be an unsubstituted alkyl such as a $C_1$-$C_{20}$ alkyl; the alkoxy can be $C_1$-$C_{20}$ alkoxy such as an unsubstituted alkoxy, $R_1$ can be a halogen, such as bromo; and each of $R_4$ and $R_5$ can be, independently, hydrogen, alkyl, or alkoxy, wherein the alkyl can be $C_1$-$C_{20}$ alkyl such as an unsubstituted alkyl, and the alkoxy can be $C_1$-$C_{20}$ alkoxy such as an unsubstituted alkoxy. In some aspects, the compounds of Formula Ic, at least one of $R_4$ and $R_5$ can be a hydrogen.

In some other aspects, an α-adrenergic agonist can have a structure set forth in Formula Id:

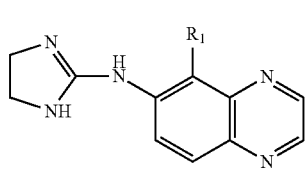

Id wherein $R_1$ is hydrogen, halogen, alkyl, or alkoxy, wherein the alkyl can be an unsubstituted alkyl such as a $C_1$-$C_{20}$ alkyl, and the alkoxy can be an unsubstituted alkoxy such as a $C_1$-$C_{20}$ alkoxy. In some aspects, $R_1$ can be a halogen, such as bromo.

In some other aspects, an α-adrenergic agonist can have a structure set forth in Formula II:

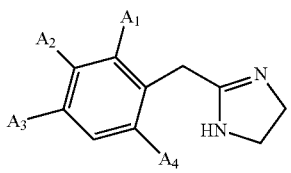

II wherein each of $A_1$, $A_3$, and $A_4$ is independently hydrogen or alkyl, and $A_2$ is hydrogen or hydroxyl.

In some other aspects, an α-adrenergic agonist can have a structure set forth in Formula III:

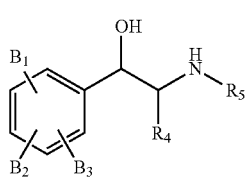

III wherein each of $B_1$, $B_2$, and $B_3$ is independently hydrogen, hydroxy, or methoxy; each of $B_4$ and $B_5$ is independently hydrogen or alkyl, wherein the alkyl can be an unsubstituted alkyl such as a $C_1$-$C_{20}$ alkyl, and wherein a substituent designated with a line segment extending into a ring structure indicates that the substitutent can attach to the ring at any available position on the ring.

The compounds of the present teachings can be prepared in accordance with well-known synthetic procedures, for example, using the general synthetic procedures set forth in U.S. Pat. No. 3,890,319 (issued Jun. 17, 1975) and U.S. Pat. No. 4,029,792 (issued Jun. 14, 1977) both of which are hereby incorporated herein by reference. Scheme 1 below illustrates one method to synthesize compounds of Formula I.

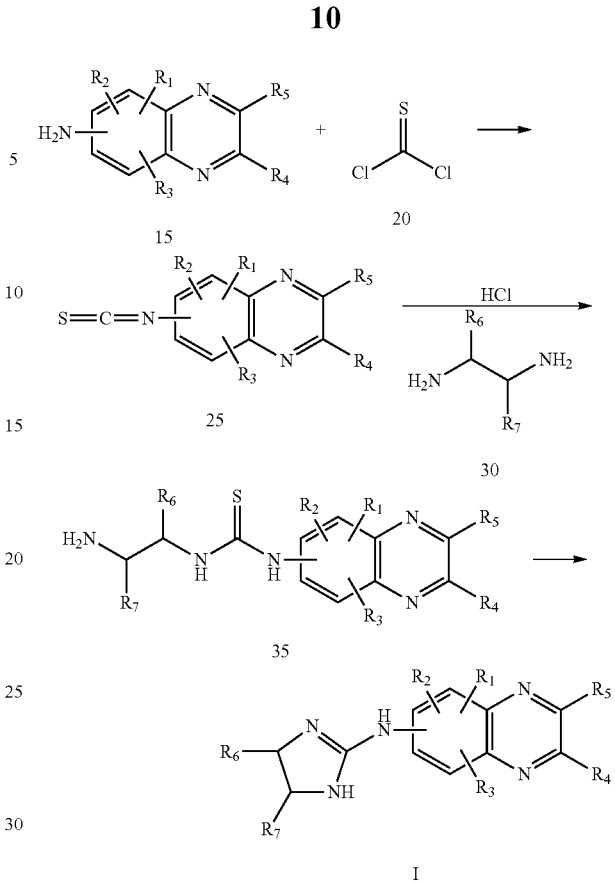

Compounds of the present teachings can be synthesized by reaction of the appropriate quinoxalines 15 with thiophosgene 20 to form corresponding isothiocyanates 25. The reaction with thiophosgene can be carried out in aqueous solution or in dilute aqueous hydrochloric acid at room temperature in a period of about 2 hours. Alternatively, the thiophosgene 20 dissolved in a water-immiscible solvent, such as chloroform, can be added to a basic aqueous solution (sodium carbonate) of quinoxalines 15 and stirred for about two hours. In the first alternative, isothiocyanates 25 precipitate from the reaction mixture. Precipitation can be completed by neutralization with excess aqueous base. Precipitated isothiocyanates 25 can be recovered by filtration and dissolved in a suitable solvent, e.g., chloroform, to form a solution. The solution can be dried (e.g., over $MgSO_4$), filtered, and concentrated to yield the isothiocyanates 25.

Isothiocyanates 25 can be treated with an excess of the appropriately substituted ethylene diamine to form the corresponding 3-quinoxalin-6-yl-thioureas 35. Isothiocyanates 25 can be reacted with an excess (e.g., 5 moles to 1 mole) of ethylene diamine 30 in a suitable solvent, e.g., diethyl ether, benzene, chloroform or dioxane. The reaction can be carried out at room temperature for about 2 hours. 3-Quinoxalin-6-yl-thioureas 35 precipitate and can be recovered by filtration and washing the filter cake with solvent.

Cyclization of 3-quinoxalin-6-yl-thioureas 35 to afford compounds of the present teachings 10 can be effected by heating a suspension of thioureas 35 with mercuric or cupric oxide in a suitable organic solvent, e.g., ethanol. The mercuric or cupric oxide can be replaced by an organic soluble mercuric or cupric salt, e.g., mercuric or cupric acetate. The reaction mixture can be filtered, to remove the mercuric or cupric sulfide by-product, and the filtrate can be concentrated to give compounds 10 in crude form. Compounds 10 can be recrystallized as the free base or converted to an acid-addition salt by conventional reaction with a suitable acid. In certain cases, cyclization can be effected by simply refluxing the thioureas 35 in a suitable organic solvent, e.g., methanol, in the absence of mercuric or cupric oxide.

Quinoxalines 15 can be synthesized by well-known synthetic procedures, for example, procedures disclosed in J. A. JOULE ET AL., HETEROCYCLIC CHEMISTRY 189-224 (3rd ed. 1995), hereby incorporated herein by reference.

Topical Formulations

In certain aspects, compounds of the present teachings can be delivered to the affected area of the skin in a pharmaceutically acceptable topical carrier. As used herein, a pharmaceutically acceptable topical carrier can be any pharmaceutically acceptable formulation that can be applied to the skin surface for topical, dermal, intradermal, or transdermal delivery of a pharmaceutical or medicament. The combination of a pharmaceutically acceptable topical carrier and a compound of the present teachings is termed a topical formulation. Topical formulations can be prepared by mixing a compound of the present teachings with a topical carrier according to well-known methods in the art, for example, methods provided by standard reference texts such as, REMINGTON: THE SCIENCE AND PRACTICE OF PHARMACY 1577-1591, 1672-1673,866-885(Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

A topical carrier useful for topical delivery of compounds of the present teachings can be any carrier known in the art for topically administered pharmaceuticals, for example, but not limited to, pharmaceutically acceptable solvents, such as a polyalcohol or water; emulsions (either oil-in-water or water-in-oil emulsions), such as creams or lotions; foams; micro emulsions; gels; ointments; liposomes; powders; and aqueous solutions or suspensions.

Emulsions, Gels, and Ointments as Topical Carriers

In some aspects, a topical carrier used to deliver a compound of the present teachings can be an emulsion, gel, or ointment. Emulsions, such as creams and lotions are suitable topical formulations for use in the present teachings. An emulsion, as used herein, is defined as a dispersed system comprising at least two immiscible phases, one phase dispersed in the other as droplets ranging in diameter from about 0.05 micron to about 100 microns. In some aspects, an emulsion can further comprise an emulsifying agent.

Emulsions, such as creams and lotions that can be used as topical carriers and their preparation are disclosed in REMINGTON: THE SCIENCE AND PRACTICE OF PHARMACY 282-291 (Alfonso R. Gennaro ed. 19th ed. 1995), hereby incorporated herein by reference.

In some other aspects, a topical carrier used to deliver an α-adrenergic receptor agonist, a prod rug thereof, a pharmaceutically acceptable salt thereof, a hydrate thereof, a solvate thereof, or a combination thereof can be a gel, such as a two-phase gel or a single-phase gel. Gels are defined herein as semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the are disclosed in REMINGTON: THE SCIENCE AND PRACTICE OF PHARMACY 1517-1518 (Alfonso R. Gennaro ed. 19th ed. 1995), hereby incorporated herein by reference. Other suitable gels are disclosed in U.S. Pat. No. 6,387,383 (issued May 14, 2002); U.S. Pat. No. 6,517,847 (issued Feb. 11, 2003); and U.S. Pat. No. 6,468,989 (issued Oct. 22, 2002), each of which patents is hereby incorporated herein by reference.

In some aspects, a composition of the present teachings can comprise a polymer thickener (gelling agent). A polymer thickener can be any polymer known to skilled artisans. Non-limiting examples of polymer thickeners include hydrophilic and hydroalcoholic gelling agents, such as those used in the cosmetic and pharmaceutical industries. Some non-limiting examples of a hydrophilic or hydroalcoholic gelling agent include "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), and "STA-BILEZE®" (ISP Technologies, Wayne, N.J.). In some aspects, the gelling agent can comprise between about 0.2% to about 4% by weight of the composition. More particularly, the compositional weight percent range for "CARBOPOL®" can be between about 0.5% w/w to about 2% w/w, while the weight percent range for "NATROLSOL®" and "KLUCEL®" can be between about 0.5% to about 4%. In various configurations, the compositional weight percent range for both "HYPAN®" and "STABILEZE®" can be between 0.5% w/w to about 4% w/w.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other examples of gelling polymers include hydroxyethylcellulose, cellulose gum, MVE/MA decadiene crosspolymer, PVM/MA copolymer, or combinations thereof.

In some other aspects, a topical carrier used to deliver an α-adrenergic receptor agonist or a salt thereof can be an ointment. Ointments are defined herein as oleaginous semisolids that contain little if any water. An ointment can be hydrocarbon based, such as a wax, petrolatum, or gelled mineral oil. Various ointments are well known in the art and are disclosed in REMINGTON: THE SCIENCE AND PRACTICE OF PHARMACY 1585-1591 (Alfonso R. Gennaro ed. 19th ed. 1995), hereby incorporated herein by reference.

Aqueous Topical Formulations

In some other aspects, a topical carrier used in a topical formulation of the present teachings can be an aqueous solution or suspension. Well-known ophthalmic solutions and suspensions can be suitable topical carriers. Examples of suitable aqueous topical formulations are described in REMINGTON: THE SCIENCE AND PRACTICE OF PHARMACY 1563-1576 (Alfonso R. Gennaro ed. 19th ed. 1995), hereby incorporated herein by reference. Other examples of suitable aqueous topical carrier systems are disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun.

19, 2001); U.S. Pat. No. 6,465,464 (issued Oct. 15, 2002), all of which patents are hereby incorporated herein by reference.

In various aspects, the pH of an aqueous topical formulation can be within the range of from about 4 to about 8, or from about 6.3 to about 6.5. In some aspects, an aqueous topical formulation can further comprise a pH-stabilizing buffering agent. In some aspects, a buffering agent can be present in an aqueous topical formulation in an amount of from about 0.05% w/w to about 10% w/w. Non-limiting examples of buffering agents include acetate buffers, citrate buffers, phosphate buffers, lactic acid buffers, borate buffers, and amine buffers such as triethylamine (TEA) buffers.

In some aspects, a composition of the present teachings can include one or more tonicity-adjusting agents. Some non-limiting examples of tonicity-adjusting agents include, sodium chloride, potassium chloride, mannitol, dextrose and glycerin. In non-limiting example, a tonicity-adjusting agent can be present in an aqueous topical formulation in an amount ranging from about 0.1% w/w to about 1% w/w, such as, for example, 0.45% w/w.

In some aspects, an aqueous topical formulation can comprise one or more viscosity-adjusting agents, which can be added to yield a formulation having a viscosity in the range of from about 15 centipoise (cps) to about 25 cps. Some non-limiting examples of viscosity-adjusting agents which can be used in various compositions include polyvinyl alcohol, povidone, hydroxypropyl methyl cellulose, poloxamers, carboxymethyl cellulose, or hydroxyethyl cellulose.

In certain aspects, an aqueous topical formulation of the present teachings can further comprise a preservative, such as benzalkonium chloride or chlorine dioxide; a viscosity-adjusting agent such as polyvinyl alcohol; and a buffer system such as sodium citrate and citric acid.

Excipients

Topical formulations of the present teachings can comprise pharmaceutically acceptable excipients such as, in non-limiting example, those described in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, and can include, without limitation, protectives, adsorbents, demulcents, emollients, preservatives, antioxidants, moisturizers, buffering agents, solubilizing agents, skin-penetration agents, and surfactants.

Suitable protectives and adsorbents include, but are not limited to, dusting powders, zinc sterate, collodion, dimethicone, silicones, zinc carbonate, aloe vera gel and other aloe products, vitamin E oil, allantoin, glycerin, petrolatum, and zinc oxide.

Suitable demulcents include, but are not limited to, benzoin, hydroxypropyl cellulose, hydroxypropyl methylcellulose, and polyvinyl alcohol.

Suitable emollients include, but are not limited to, animal and vegetable fats and oils, myristyl alcohol, alum, and aluminum acetate.

Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other antimicrobial agents such as chlorhexidine, chlorocresol, benzoic acid and polymyxin. Chlorine dioxide ($ClO_2$), such as stabilized chlorine dioxide, can be used as a preservative for use with topical formulations of the present teachings. The term "stabilized chlorine dioxide" is well known in the industry and by those skilled in the art. Stabilized chlorine dioxide, as used herein, includes one or more chlorine dioxide precursors such as one or more chlorine dioxide-containing complexes and/or one or more chlorite-containing components and/or one or more other entities capable of decomposing or being decomposed in an aqueous medium to form chlorine dioxide. U.S. Pat. No. 5,424,078 (issued Jun. 13, 1995), hereby incorporated herein by reference, discloses a form of stabilized chlorine dioxide and a method for producing same, which can be used in topical formulations of the present teachings. The manufacture or production of certain stabilized chlorine dioxide products is described in U.S. Pat. No. 3,278,447, hereby incorporated herein by reference. A commercially available stabilized chlorine dioxide which can be utilized in the practice of the present methods is the proprietary stabilized chlorine dioxide of BioCide International, Inc. of Norman, Okla., sold under the trademark Puroqene" or Purite™. Other suitable stabilized chlorine dioxide products include that sold under the trademark DuraKlor by Rio Linda Chemical Company, Inc., and that sold under the trademark Antheium Dioxide by International Dioxide, Inc.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents include, but are not limited to, acetate buffers, citrate buffers, phosphate buffers, lactic acid buffers, triethanolamine, and borate buffers.

Suitable solubilizing agents include, but are not limited to, quaternary ammonium chlorides, cyclodextrins, benzyl benzoate, lecithin, and polysorbates.

Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyllaurate, glycerol monooleate, and propylene glycol monooleate); and N-methylpyrrolidone.

Topical compositions of the present invention may also contain sunscreens. An example of a sunscreen useful in the invention is titanium dioxide.

Pharmaceutical Additives

Topical formulations of the present teachings can include pharmaceutical compounds or their pharmaceutically acceptable salts, for example, but not limited to, topical corticosteroids and other anti-inflammatory agents, such as betamethasone, diflorasone, amcinonide, fluocinolone, mometasone, hydrocortisone, prednisone, and triamcinolone; local anesthetics and analgesics, such as camphor, menthol, lidocaine, and dibucaine, and pramoxine; antifungals, such as ciclopirox, chloroxylenol, triacetin, sulconazole, nystatin, undecylenic acid, tolnaftate, miconizole, clotrimazole, oxiconazole, griseofulvin, econazole, ketoconozole, and amphotericin B; antibiotics and anti-infectives, such as mupirocin, erythromycin, clindamycin, gentamicin, polymyxin, bacitracin, and silver sulfadiazine; and antiseptics, such as iodine, povidine-iodine, benzalkonium chloride, benzoic acid, chlorhexidine, nitrofurazine, benzoyl peroxide, hydrogen peroxide, hexachlorophene, phenol, resorcinol, and cetylpyridinium chloride.

Dosage

Dosages and dosing frequency can be determined by a skilled artisan such as a trained medical professional. Dosage can depend on the activity of an α-adrenergic receptor agonist, the characteristics of the particular topical formulation, and the identity and severity of the dermatologic disorder treated or prevented.

In general, an α-adrenergic receptor agonist comprised by a composition can be present in a formulation in an amount of from about 0.001% w/w up to about 10% w/w, from about 0.002% w/w up to about 1% w/w, or from about 0.0025% w/w up to about 0.5% w/w.

To ameliorate a telangiectasia, the topical formulations of the present teachings can be topically applied directly to the affected area in any conventional manner well known in the art. As used herein, "ameliorating a telangiectasia" includes lessening the severity of a telangiectasia. Lessening severity of a telangiectasia can include complete or partial disappearance of a telangiectasia, as determined by the recipient patient or an external observer.

In various aspects, a composition of the present teachings can be topically applied by any known method in the art, for example, with the aid of a dropper or applicator stick, as a mist via an aerosol applicator, via an intradermal or transdermal patch, or by simply spreading a formulation onto the affected area with fingers, a sponge, a pad, or wipes. Generally, the amount of a topical formulation applied to an affected skin area ranges from about 0.1 g/cm$^2$ to about 5 g/cm$^2$ of skin surface area, or from about 0.2 g/cm$^2$ to about 0.5 g/cm$^2$ of skin surface area. In various aspects, an application of a topical composition can noticeably ameliorate a telangiectasia within about 2 minutes following application, within about 5 minutes following application, or within about 10 minutes following application. In some aspects, a composition can be maximally effective at about 30 minutes after application, and the ameliorative effects can last up to about 2 hours, up to about 4 hours, up to about 8 hours, up to about 12 hours, up to about 18 hours, or up to about 24 hours, or longer. Accordingly, in some aspects, a composition can be topically applied to skin at a site of telangiectasia symptoms once per day, twice per day, or three or more times per day.

Use of Topical Formulations in Combination with Other Skin-Disorder Treatments

The formulations of the present teachings can be used in combination with other treatments and medications to provide more effective treatment of a telangiectasia. In some aspects, a topical formulation can be used in combination with treatment regimens and medications for treatment of dermatologic disorders, such as those disclosed in THE MERCK MANUAL 811-830 (Keryn A. G. Lane et al. eds. 17th ed. 2001), hereby incorporated herein by reference.

In some aspects, a formulation, composition or compound can be used in combination with another medicament or treatment. In some configurations, a combination can be administered to a subject in a sequence and within a time interval such that they can act together to treat or prevent formation of a telangiectasia.

Any suitable route of administration can be employed to deliver the additional treatment or medication including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation.

In one aspect, the topical formulations can be used in combination with systemic administration of antibiotics or retinoids including, but not limited to, orally dosed antibiotics, such as tetracycline, minocin, minocycline, erythromycin, and doxycycline, and orally dosed retinoids such as isotretinoins (e.g., Accutane or Roaccutance).

In other aspects, the topical formulations disclosed herein can be used in combination with other topical treatments including, but not limited to, topical formulations consisting of metronidizole, hydrogen peroxide, benzoyl peroxide, lipoic acid, and azelaic acid, and sulfur preparations; topically dosed antibiotics, such as metronidazole, clindamycin, and erythromycin; topical retinoids such as tretinoin, adapalene, tazarotene; or topical steroids.

In other aspects, topical formulations described herein can be used in combination with other therapies such as, for example, mixed light pulse therapy (photoderm), pulsed dye laser treatment, or electrosurgery.

Article of Manufacture

Certain aspects of the present teachings include an article of manufacture which comprises a topical formulation comprising at least one α-adrenergic receptor agonist, a prod rug thereof, a pharmaceutically acceptable salt thereof, a hydrate thereof, a solvate thereof or a combination thereof, in a suitable container with labeling and instructions for use. The container can be, in non-limiting example, a dropper or tube with a suitable small orifice size, such as an extended tip tube made of any pharmaceutically suitable material, or a single or multiple use pouch, such as, for example a DelPouch™ (Cardinal Health).

In various aspects, a topical formulation can be filled and packaged into a plastic squeeze bottle, tube or pouch containing pads or wipes. Suitable container-closure systems for packaging a topical formulations of the present teachings are commercially available, for example, from Wheaton Plastic Products, 1101 Wheaton Avenue, Millville, N.J. 08332.

In some configurations, a formulation can be packaged with written material, such as, for example, instructions, a pamphlet or a package label. The labeling instructions can explain how to administer a topical formulation in an amount and for a period of time sufficient to treat a telangiectasia.

EXAMPLES

The following examples are provided for illustrative purposes only and are not to be construed as limiting the present teachings' scope in any manner. The description of an article, a composition, or a method in an example does not imply that the described article or composition has, or has not, been produced, or that that the described method has, or has not, been performed, regardless of verb tense.

Example 1

This example illustrates synthesis of (5-Bromo-quinoxalin-6-yl)-(4,5-dihydro-1H-imidazol-2-yl)-amine.

To a stirred solution of 6-amino-5-bromoquinoxaline hydrobromide (10 g) in distilled water (150 ml) is added thiophosgene (3 ml). The solution is stirred for two hours at room temperature and the resultant precipitate is collected by filtration, washed with water, and dried to afford 5-bromo-6-isothiocyanato-quinoxaline.

The 5-bromo-6-isothiocyanato-quinoxaline (3.5 g.) is directly dissolved in benzene (400 ml) and added dropwise to a well-stirred solution of ethylene diamine (15 g.) in benzene (50 ml). During a period of about two hours, an oil separates as a lower layer. The upper benzene layer is poured off and the oil is washed with diethyl ether and then dissolved in methanol (500 ml). The methanolic solution is refluxed until hydrogen sulfide evolution ceases. The methanolic solution is concentrated in vacuo to a volume of approximately 100 ml upon which a yellow solid precipitates. The precipitate is collected by filtration and recrystallized from methanol to afford of (5-Bromo-quinoxalin-6-yl)-(4,5-dihydro-1H-imidazol-2-yl)-amine: m.p. 250-251 C.

Example 2

This example illustrates an aqueous topical formulation.

An aqueous solution topical formulation comprises (5-Bromo-quinoxalin-6-yl)-(4,5-dihydro-1H-imidazol-2-yl)-amine-L-tartrate (brimonidine tartrate) (0.15% w/w); Puriteg (0.005% w/w) (stabilized chlorine dioxide) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

Example 3

This example illustrates a second aqueous topical formulation.

An aqueous solution topical formulation comprises (5-Bromo-quinoxalin-6-yl)-(4,5-dihydro-1H-imidazol-2-yl)-amine-L-tartrate, (brimonidine tartrate) (0.15% w/w); benzalkonium chloride (0.005% w/w.) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

Example 4

This example illustrates a cream topical formulation.
A cream topical formulation is described in Table 1 below.

TABLE 1

Cream Topical Formulation (Hydrophilic Ointment)

| Ingredient | Weight Percent |
|---|---|
| Brimonidine tartrate | 0.15% |
| Stearic acid | 7% |
| Stearyl alcohol | 5% Cetyl alcohol |
| 2% Glycerin | 10% |
| Sodium lauryl sulfate | 1% |
| Propylparaben | 0.05% |
| Methylparaben | 0.25% |
| Disodium edetate | 0.055 |
| Distilled water | QS |

To make the formulation, the stearyl alcohol and the white petrolatum were melted on a steam bath, and warmed to about 75 degrees C. The other ingredients, previously dissolved in the water and warmed to 75 degrees C., were then added, and the mixture was stirred until it congealed. The mixture was then allowed to cool with stirring, and brimonidine tartrate was then added as a concentrated solution. {confirm that this is an actual working example}

Example 5

This example illustrates an ointment topical formulation.
An ointment topical formulation is described in Table 2 below.

TABLE 2

Ointment Formulation (Hydrophilic Ointment)

| Ingredients | Weight |
|---|---|
| Brimonidine tartrate | 10 g |
| Cholesterol | 30 g |
| Stearyl Alcohol | 30 g |
| White Wax | 80 g |
| White Petrolatum | 850 g |

To make the formulation, the stearyl alcohol and white wax were mixed together on a steam bath. The cholesterol was then added and stirred until it completely dissolved. The white petrolatum was then added and mixed. The mixture was removed from the bath, and stirred until it congealed. With continuous stirring, brimonidine tartrate was added as a concentrated slurry. {confirm that this is an actual working example Example 6

This example illustrates a gel formulation.
A gel formulation is described in table 3 below.

TABLE 3

Gel Formulation

| Ingredients | Weight % |
|---|---|
| Brimonidine tartrate | 1.0% |
| Methylparaben NF | 0.15% |
| Propylparaben NF | 0.03% |
| Hydroxyethylcellulose NF | 1.25% |
| Disodium Edetate USP | 0.05% |
| Purified Water, USP | QS 100% |

Example 7

This example illustrates a second gel formulation.
A gel formulation is described in Table 4 below.

TABLE 4

Gel Formulation

| Ingredients | Weight % |
|---|---|
| Brimonidine tartrate | 1.0% |
| Methylparaben | 0.20% |
| Propylparaben | 0.05% |
| Carbomer 934P NF | 1.0% |
| Sodium Hydroxide | QS pH 7 |
| Purified Water USP | QS 100% |

The ingredients are mixed together and aqueous sodium hydroxide is slowly added to the mixture until a pH of about 7 is reached and the gel is formed.

Example 8

This example illustrates a gel third formulation.
A gel formulation is described in Table 5 below.

TABLE 5

Gel Formulation

| Ingredients | Weight % |
|---|---|
| Brimonidine tartrate | 1.0% |
| Methylparaben | 0.2% |
| Propylparaben | 0.05% |
| "CARBOPOL ®" | 1.0% |
| Triethanolamine | QS pH 7 |
| Water | QS 100% |

The ingredients are mixed together and stirred. Triethanolamine is added until a pH of about 7 is attained.

Example 9

This example illustrates a foam formulation.
A foam formulation is described in Table 6 below.

TABLE 6

Foam Formulation

| Ingredients | Amount (Weight %) |
|---|---|
| Brimonidine tartrate | 0.2 |
| Stearic Acid | 4.2 |
| Laureth-23 | 1.4 |
| Sodium Lauryl Sulfate | 0.5 |
| Triethanolamine | 2.2 |
| Butylated hydroxytoluene (BHT) | 0.01 |
| Fragrance | 0.5 |
| Aeron A-31 Propellant | 3 |
| Water | 87.99 |

The water is heated to 80-85° C., after which stearic acid is added. Once the stearic acid is melted, the laureth-23 is added, melted, and mixed well. Next, triethanolamine is added and the resulting composition is mixed well for about 30 minutes to form a soap. The resulting soap is then cooled to about 65° C., after which sodium lauryl sulfate is added. The composition is then mixed well. Next, the BHT and the Brimonidine tartrate are added, followed by mixing. The resulting composition is then cooled to room temperature and the fragrance added. The product is packaged with the Aeron A-31 propellant in an aerosol can using conventional techniques and mechanically shaken for 5 minutes. The product dispenses as a cone-shaped spray that deposits onto the skin as a layer of rich lather that quickly covers a wide area of skin, and begins to relieve symptoms within about 2 minutes after application.

Examples 10-13

These examples illustrates additional foam formulations.
Additional foam formulations are described in Table 7 below.

TABLE 7

Foam Formulations

| | Amount (Weight %) | | | |
|---|---|---|---|---|
| Ingredients | Example 10 | Example 11 | Example 12 | Example 13 |
| Brimonidine tartrate | 0.1 | 0.15 | 0.2 | 0.25 |
| Stearic Acid | 6.3 | 5.0 | 3.6 | 3.1 |
| Laureth-23 | 2.1 | 1.7 | 1.2 | 1.0 |
| Sodium Lauryl Sulfate | 0.8 | 0.6 | 0.5 | 0.4 |
| Triethanolamine | 3.2 | 2.6 | 1.9 | 1.6 |
| Butylated hydroxytoluene (BHT) | 0.02 | 0.02 | 0.01 | 0.01 |
| Fragrance | 0.5 | 0.5 | 0.5 | 0.5 |
| Aeron A-31 Propellant | 3 | 3 | 3 | 3 |
| Water | 83.98 | 86.43 | 89.09 | 90.14 |

Preparation: these foam formulations are prepared and packaged as in Example 9. In each case, the product dispenses as a cone-shaped spray that deposits onto the skin as a layer of rich lather that quickly covers a wide area of skin, and begins to relieve symptoms within about 2 minutes after application.

Example 14

This example illustrates an additional foam formulation.
An additional foam formulation is described in Table 8 below.

TABLE 8

Foam Formulation

| Ingredient | Amount (Weight %) |
|---|---|
| Brimonidine tartrate | 0.2 |
| Water | 91.11 |
| Palmitic Acid | 2.12 |
| Laureth-23 | 0.93 |
| Triethanolamine (99%) | 1.13 |
| Cetyl Dimethicone Copolyol | 0.19 |
| Mineral Oil | 0.31 |
| Stearyl Alcohol | 0.31 |
| Lauramide DEA | 0.15 |
| PEG-150 Distearate | 0.05 |
| Imidazolidinyl Urea | 0.0016 |
| Methylparaben | 0.0005 |
| Propylparaben | 0.00003 |
| Freeze Dried Aloe Powder | 0.0015 |
| Fragrance | 0.50 |
| Aeron A-31 Propellant | 3.00 |

The aqueous phase is prepared as follows. The water is heated to 80° C., after which palmitic acid is added. Once the palmitic acid is melted, the laureth-23 is added, melted, and mixed well. Next, triethanolamine is added and the resulting composition is mixed well for about 15 minutes to form a soap.

Stearyl alcohol, mineral oil, lauramide DEA, cetyl dimethicone copolyol, PEG-150 distearate, and BHT are mixed and heated at 55° C. to form the oil phase. The oil phase is combined with the aqueous phase at 80° C. and mixed well for about 15 minutes. The resulting mixture is then cooled to room temperature and the imidazolidinyl urea, methylparaben, and propylparaben are added, and then mixed well. The brimonidine tartrate is then added, and mixed well. Next, the fragrance is added, followed by gentle mixing. The aloe is then dissolved in make-up water and added with slow mixing to form the product formulation which is then packaged in an aerosol can as described in Example 9.

The product dispenses as a cone-shaped spray that deposits onto the skin as a layer of rich lather that quickly covers a wide area of skin, and begins to relieve symptoms within about 2 minutes after application.

Example 15

This example illustrates an additional foam formulation.
An additional, non-soapy foam formulation is described in Table 9 below.

TABLE 9

Foam Formulation

| Ingredient | Amount (Weight %) |
|---|---|
| Brimonidine tartrate | 0.2 |
| Ethanol | 6 |
| Ethyl Ester of PVM/MA | 4 |
| Copolymer Dimethicone Copolyol | 0.1 |
| Water | 80.37 |
| PVPN A Copolymer | 1 |
| Sodium Lauryl Sulfate | 1 |
| Oleth-20 | 0.5 |
| Cocamide MEA | 0.05 |
| Methyl Paraben | 0.1 |
| Aminomethyl Propanol | 0.53 |
| Stearalkonium Chloride | 0.05 |
| Steareth-16 | 0.1 |
| Panthenol | 0.5 |
| Fragrance | 0.5 |
| Aeron A-46 | 5 |

The alcohol phase is prepared by dissolving ethyl ester of PVM/MA copolymer in ethanol, after which dimethicone is added and mixed well. The aqueous phase is prepared by heating the water to 65° C., after which the PVPN A copolymer is added and mixed well. The oil phase is prepared by mixing the Oleth-20, cocamide MEA, and steareth-16 at 60° C. to form a blend. The oil phase is then added to the aqueous phase at 65° C. and mixed well. Next, the methylparaben is added to the mixture, followed by mixing, after which the aminomethyl propanol, stearalkonium chloride, and panthenol are added and mixed until uniform. The resulting composition is cooled to room temperature, after which the alcohol phase is added and mixed well. The fragrance is then added and mixed gently to form the product. The product is then packaged in an aerosol can.

The product dispenses as a cone-shaped spray that deposits onto the skin as a layer of rich lather that quickly covers a wide area of skin, and begins to relieve symptoms within about 2 minutes after application.

Example 16

This example illustrates treatment of a telagiectasia of a subject by topical application of an α-adrenergic receptor agonist.

In this example, a 59 year old woman with facial telangiectasias cleanses her face using ordinary soap and water cleaning. After toweling her face dry and further air drying, she uses a cotton swab to apply topically Alphagan" ® P (Allergan) (0.15% brimonidine tartrate in isotonic saline and citrate buffer, pH 6.3-6.5) directly to the telangiectatic skin. As observed without magnification, the telangiectasias in the swabbed area begin to fade in visibility within about 15 minutes after application of the Alphagan" ® P, and become nearly entirely faded within about 30 minutes. The telangiectasias remain faded for about 18 hr.

Example 17

This example illustrates treatment of a telagiectasia of a subject by topical application of an α-adrenergic receptor agonist.

In this example, a 56 year old male has small spider veins on both cheeks on his face. He applies a few drops of Alphagan" ® P onto each cheek and distributes it using his fingertips. He begins to see relief of his spider veins within 10 minutes. He considers the spider veins to be imperceptible within about 30 minutes. The effects last about 24 hours in this individual.

Example 18

This example illustrates treatment of a telagiectasia of a subject by topical application of an α-adrenergic receptor agonist.

In this example, an adult female has extensive spider veins on her chin. She applies topically a solution comprising brimonidine to the skin on her chin, using cotton to. The spider veins become imperceptible within 30 minutes, much to the delight of the subject. The effects last at least 18 hour in this individual.

Definitions

The phrase "pharmaceutically acceptable salt(s)", as used herein, means those salts of compounds of the present teachings that are safe and effective for topical use in mammals and that possess the desired biological activity. Pharmaceutically acceptable salts include salts of acidic or basic groups present in compounds of the present teachings. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds disclosed herein can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCl. 1-19 (1977), incorporated herein by reference.

The term "pharmaceutically acceptable topical formulation" as used herein means any formulation which is pharmaceutically acceptable for topical delivery of a compound. A "topical formulation" can comprise at least a compound of the present disclosure. The choice of topical formulation will depend on several factors, including the nature of the symptoms to be treated or prevented, the physiochemical characteristics of the particular compound of the present teachings and of other excipients present, their stability in the formulation, available manufacturing equipment, and cost constraints.

As used herein, the term "prodrug" refers to a drug precursor which is inactive but can be activated by a biological or biochemical process, such as, for example, enzymatic hydrolysis.

As used herein, a "therapeutically effective amount" of a compound means an amount of the compound that is effective to ameliorate a telangiectasia.

As used herein, the term "subject" means any animal, such as a mammal, to which will be or has been administered compounds or topical formulations of the present teachings. The term "mammal" as used herein, encompasses any mammal. Examples of mammals include, but are not limited to, cows, horses, sheep, pigs, cats, dogs, mice, rats, rabbits, guinea pigs, monkeys, and humans.

The term "analog" refers to a chemical compound that is structurally similar to a parent compound and has chemical properties or pharmaceutical activity in common with the parent compound. Analogs include, but are not limited to, homologs, i.e., where the analog differs from the parent compound by one or more carbon atoms in series; positional isomers; compounds that differ by interchange of one or more atoms by a different atom, for example, replacement of a carbon atom with an oxygen, sulfur, or nitrogen atom; and compounds that differ in the identity of one or more functional groups, for example, the parent compound differs from its analog by the presence or absence of one or more suitable substituents. Suitable substituents include, but are not limited to, $(C_1-C_8)$alkyl; $(C_1-C_8)$alkenyl; $(C_1-C_8)$alkynyl: aryl; $(C_2-C_5)$heteroaryl; $(C_1-C_6)$heterocycloalkyl; $(C_3-C_7)$cycloalkyl; O—$(C_1-C_8)$alkyl; O—$(C_1-C_8)$alkenyl; O—$(C_1-C_8)$alkynyl; O-aryl; CN; OH; oxo; halo, C(O)OH; COhalo; O(CO)halo; $CF_3$, $N_3$; $NO_2$, $NH_2$; NH$((C_1-C_8)$alkyl); N$((C_1-C_8)$alkyl$)_2$; NH(aryl); N(aryl)$_2$ N$((C_1-C_8)$alkyl)(aryl); (CO)$NH_2$; (CO)NH$((C_1-C_8)$alkyl); (CO)N$((C_1-C_8)$alkyl$)_2$; (CO)NH(aryl); (CO)N(aryl)$_2$; O(CO)$NH_2$; NHOH; NOH$((C_1-C_8)$alkyl); NOH(aryl); O(CO)NH$((C_1-C_8)$alkyl); O(CO)N$((C_1-C_8)$alkyl$)_2$; O(CO)NH(aryl); O(CO)N(aryl)$_2$; CHO; CO$((C_1-C_8)$alkyl); CO(aryl); C(O)O$((C_1-C_8)$alkyl); C(O)O(aryl); O(CO)$((C_1-C_8)$alkyl); O(CO)(aryl); O(CO)O$((C_1-C_8)$alkyl); O(CO)O(aryl); S—$(C_1-C_8)$alkyl; S—$(C_1-C_8)$alkenyl; S—$(C_1-C_8)$alkynyl; S-aryl; S(O)—$(C_1-C_8)$alkyl; S(O)—$(C_1-C_8)$alkenyl; S(O)—$(C_1-C_8)$alkynyl; and S(O)-aryl; S(O)$_2$—$(C_1-C_8)$alkyl; S(O)$_2$—$(C_1-C_8)$alkenyl; S(O)$_2$—$(C_1-C_8)$alkynyl; and S(O)$_2$-aryl. One of skill in the art can readily choose a suitable substituent based upon the stability and pharmacological activity of a compound.

The term "alkyl" means a saturated, monovalent, unbranched or branched hydrocarbon chain. Examples of alkyl groups include, but are not limited to $(C_1-C_3)$alkyl groups, such as methyl, ethyl, propyl, isopropyl and $(C_4-C_8)$ alkyl groups, such as 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl -1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, heptyl, and octyl. An alkyl group can be unsubstituted or substituted with one or two suitable attachments.

The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_8)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkynyl" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_8)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

The term "aryl" means a monocyclic or polycyclic-aromatic group comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. In some aspects, an aryl group can be a monocyclic ring, wherein the ring comprises 6 carbon atoms, referred to herein as "$(C_6-)$aryl".

The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. As is well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$heteroaryl".

The term "cycloalkyl" means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes and $(C_3-C_7)$cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents. Preferably, the cycloalkyl group is a monocyclic ring or bicyclic ring.

The term "heterocycloalkyl" means a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 2 to 6 carbon atoms and from 1 to 3 heteroatoms, referred to herein as $(C_1-C_6)$heterocycloalkyl.

The term "halogen" means fluorine, chlorine, bromine, or iodine. Correspondingly, the term "halo" means fluoro, chloro, bromo, and iodo.

As used herein, the terms "treatment" and "treating" refer to an amelioration or reversal of a disease or disorder, or at least one discernible sign or symptom thereof. In some aspects, "treatment" or "treating" can refer to an amelioration or reversal of at least one measurable physical parameter related to the disease or disorder being treated, not necessarily discernible by the subject. "Treatment" or "treating" can also refer to inhibiting or slowing the progression of a disease or disorder, either physically, e.g., stabilization of a discernible symptom, physiologically, e.g., stabilization of a physical parameter, or both.

As used herein, an "effective amount" of an α-adrenergic receptor agonist is an amount effective to treat telangiectasia, i.e. reduce locally the visibility of the dilated blood vessels following topical administration. The amount of the αadrenergic receptor agonist in a topical formulation will vary depending upon which alpha agonist is employed but can be in the range of about 0.001% w/w up to about 10% w/w of the formulation. In various aspects, the amount administered can be an amount that covers the affected area. In certain aspects, covering an affected area can comprise applying a formulation to affected skin manually, by dabbing or brushing on with an applicator, which can be any type of applicator known to skilled artisans, such as, in non-limiting example, a cotton-tipped stick.

As used herein, "carbomer" is the USP designation for various polymeric acids that are dispersible but insoluble in water. When the acid dispersion is neutralized with a base a clear, stable gel is formed. Carbomer 934P is physiologically inert and is not a primary irritant or sensitizer. Other carbomers include 910, 940, 941, and 1342.

In certain aspects, the present teachings disclose methods of treating a telangiectasia, comprising topically administering to the skin of a subject in need of such treatment a compound of a formula:

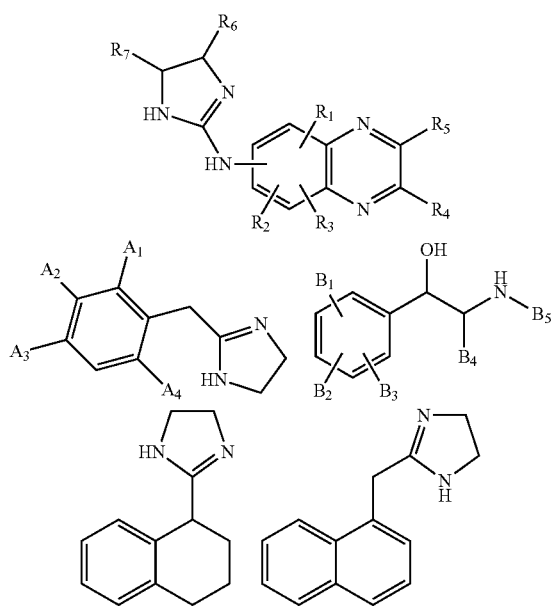

wherein each of $R_1$, $R_2$, and $R_3$ is independently hydrogen, halogen, alkyl, or alkoxy; each of $R_4$ and $R_5$ is independently hydrogen, alkyl, or alkoxy; and each of $R_6$ and $R_7$ is independently hydrogen, nitro, alkyl, or alkoxy; wherein each of $A_1$, $A_3$, and $A_4$ is independently hydrogen or alkyl; and $A_2$ is independently hydrogen or hydroxy; and wherein each of $B_1$, $B_2$, and $B_3$ is independently hydrogen, hydroxy, or alkoxy; and each of $B_4$ and $B_5$ is independently hydrogen or alkyl, and wherein a substituent designated with a line segment extending into a ring structure can attach to the ring at any available position on the ring. In various aspects, an alkyl can be an unsubstituted alkyl such as a $C_1$-$C_{20}$ alkyl, and the alkoxy can be an unsubstituted alkoxy such as a $C_1$-$C_{20}$ alkoxy.

All citations (e.g., scientific journal publications, patents, and other reference material) mentioned herein are hereby incorporated herein by reference to the same extent as if each individual citation was specifically and individually indicated to be incorporated by reference. One of ordinary skill in the art can make many variations and modifications to the above-described aspects of the present teachings without departing from the spirit or scope of the appended claims. Accordingly, all such variations and modifications are within the scope of the appended claims. In addition, specific examples and aspects described above are illustrative only and are not intended to limit the scope of the claims.

What is claimed is:

1. A topical dermal composition comprising:
   a therapeutically effective amount of brimonidine or a pharmaceutically acceptable salt thereof;
   titanium dioxide; and
   a pharmaceutically acceptable carrier selected from the group consisting of sprays, mists, aerosols, lotions, gels, creams, pastes, and emulsions, wherein the composition is suitable for application to skin.

2. The topical composition according to claim 1, wherein the pH value of the composition is in the range of about 5 to 8.

3. The topical composition according to claim 1, wherein the pharmaceutically acceptable carrier is an aqueous gel.

4. The topical composition according to claim 3, wherein the brimonidine or a pharmaceutically acceptable salt thereof is present in an amount in the range of about 0.01 to 5 weight percent.

5. The topical composition according to claim 3, wherein the pH value of the composition is in the range of about 5 to 8.

6. The topical composition according to claim 3, further comprising a preservative.

7. The topical composition according to claim 3, further comprising a local anesthetic.

8. The topical composition according to claim 3, further comprising a skin humectant.

9. The topical composition according to claim 3, wherein the aqueous gel comprises water, and a water-gelling amount of a pharmaceutically acceptable gelling agent selected from the group consisting of carbomers, glycerine polyacrylate, and mixtures thereof.

10. The topical composition according to claim 1, wherein the pharmaceutically acceptable carrier is a cream.

11. The topical composition according to claim 10, wherein the brimonidine or a pharmaceutically acceptable salt thereof is present in an amount in the range of about 0.01 to 5 weight percent.

12. The topical composition according to claim 10, wherein the pH value of the composition is in the range of about 5 to 8.

13. The topical composition according to claim 10, further comprising a preservative.

14. The topical composition according to claim 10, further comprising a local anesthetic.

15. The topical composition according to claim 10, further comprising a skin humectant.

16. The topical composition according to claim 10, wherein the cream comprises stearic acid, stearyl alcohol, cetyl alcohol, glycerin, and water.

17. A topical dermal composition comprising:
a therapeutically effective amount of an active agent consisting of brimonidine or a pharmaceutically acceptable salt thereof;
titanium dioxide; and
a pharmaceutically acceptable carrier selected from the group consisting of sprays, mists, aerosols, lotions, gels, creams, ointments, pastes, unguents, and emulsions.

18. A container suitable for delivering a topical formulation comprising therein a therapeutically effective amount of brimonidine or a pharmaceutically acceptable salt thereof, titanium dioxide, and a pharmaceutically acceptable carrier selected from the group consisting of sprays, mists, aerosols, lotions, gels, creams, pastes, and emulsions.

19. The container according to claim 18, wherein the carrier is a gel or cream and the container is a squeeze bottle or tube.

20. A topical dermal composition comprising:
a therapeutically effective amount of brimonidine or a pharmaceutically acceptable salt thereof;
titanium dioxide; and
a pharmaceutically acceptable carrier selected from the group consisting of sprays, mists, aerosols, lotions, gels, creams, pastes, and emulsions, wherein the composition is limited to facial and non-ophthalmic topical application.

21. A topical dermal composition comprising:
a therapeutically effective amount of an active agent consisting of brimonidine or a pharmaceutically acceptable salt thereof;
titanium dioxide; and
a pharmaceutically acceptable carrier selected from the group consisting of sprays, mists, aerosols, lotions, gels, creams, ointments, pastes, unguents, and emulsions, wherein the composition is limited to facial and non-ophthalmic topical application.

22. A container suitable for delivering a topical formulation comprising therein a therapeutically effective amount of brimonidine or a pharmaceutically acceptable salt thereof, titanium dioxide, and a pharmaceutically acceptable carrier selected from the group consisting of sprays, mists, aerosols, lotions, gels, creams, pastes, and emulsions, wherein the composition is limited to facial and non-ophthalmic topical application.

* * * * *